United States Patent [19]

Grimm et al.

[11] Patent Number: 4,936,827
[45] Date of Patent: Jun. 26, 1990

[54] IMPLANTER APPLICATOR

[75] Inventors: C. Louis Grimm, Shawnee, Kans.; Irving V. Sollins, Cuernavaca, Mexico

[73] Assignee: Ivy Laboratories, Inc., Overland Park, Kans.

[21] Appl. No.: 179,985

[22] Filed: Apr. 11, 1988

[51] Int. Cl.⁵ ............................................. A61D 7/00
[52] U.S. Cl. ................................... 604/60; 604/239; 604/240
[58] Field of Search ...................... 604/57–64, 604/187, 218, 239–243, 272; 606/117

[56] References Cited

U.S. PATENT DOCUMENTS

| | | | |
|---|---|---|---|
| 1,789,766 | 1/1931 | Muir | 604/64 |
| 2,020,111 | 11/1935 | Eisele | 604/242 |
| 2,577,556 | 12/1951 | Williams | 604/241 |
| 2,632,444 | 3/1953 | Kas | 604/62 |
| 2,727,514 | 12/1955 | Lockhart | 604/242 |
| 2,761,446 | 9/1956 | Reed | 604/59 |
| 3,016,895 | 1/1962 | Sein | 604/60 |
| 3,294,089 | 12/1966 | Brookfield | 604/241 |
| 4,263,910 | 4/1981 | Pardekooper et al. | 604/60 |
| 4,451,253 | 5/1984 | Harman | 604/60 |
| 4,490,142 | 12/1984 | Silvern | 604/241 |
| 4,787,384 | 11/1988 | Campbell et al. | 604/60 |

FOREIGN PATENT DOCUMENTS 0152062  8/1985  European Pat. Off. ............ 604/272

Primary Examiner—Stephen C. Pellegrino
Assistant Examiner—Ralph Lewis
Attorney, Agent, or Firm—Morris Fidelman; Franklin D. Wolffe

[57] ABSTRACT

A medicament implanter system which comprises:
a single use needle pre-charged with medicament;
a cartridge wherein a multiplicity of pre-charged needles may be packaged; and
an implanter applicator instrument adapted to remove a pre-charged needle from the cartridge, and to reinsert a used needle into the cartridge.

The applicator instrument is constructed so that a needle positioned therein is locked in properly oriented position for expulsion of the medicament upon operation of an impeller which forms part of the applicator instrument.

6 Claims, 4 Drawing Sheets

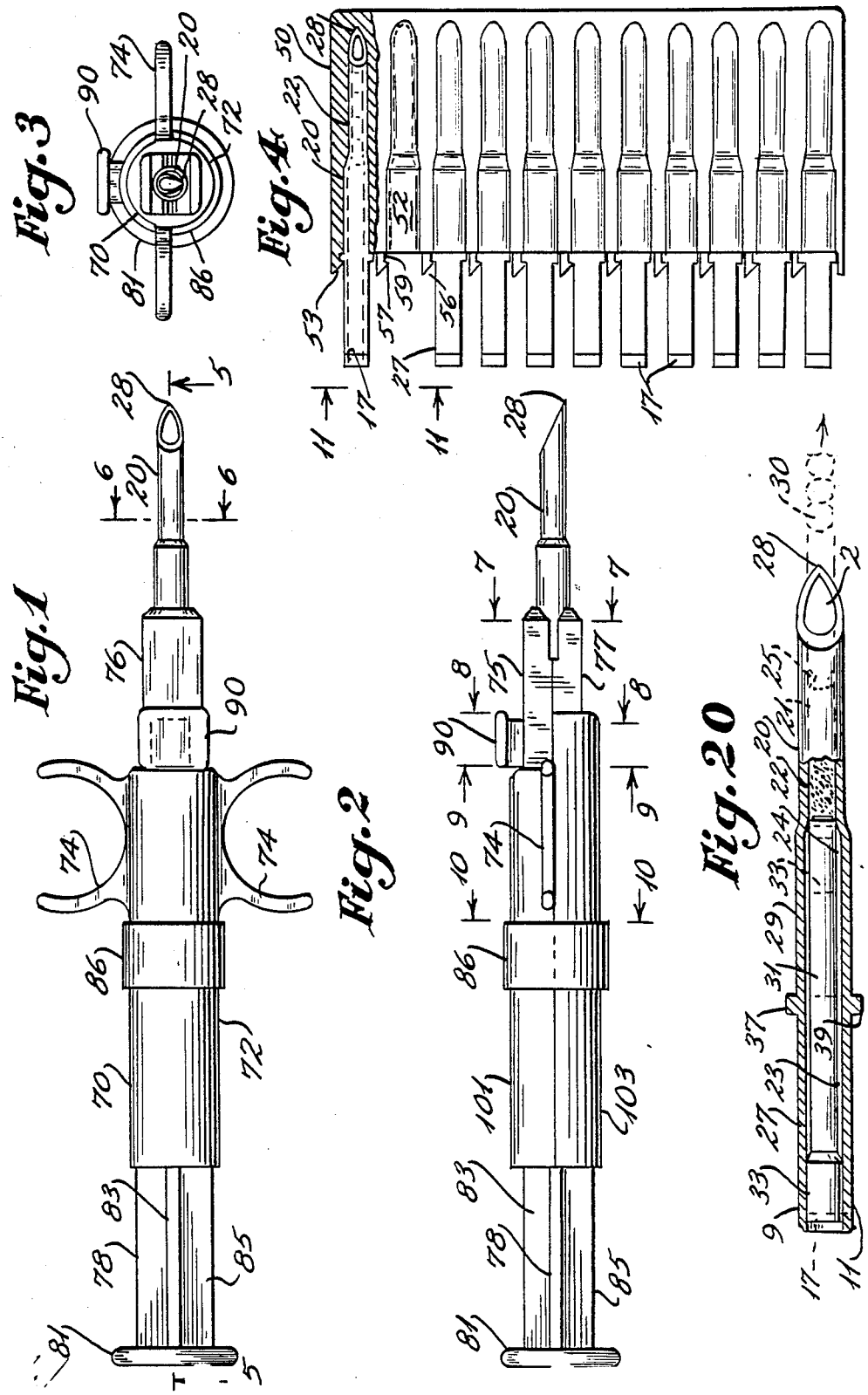

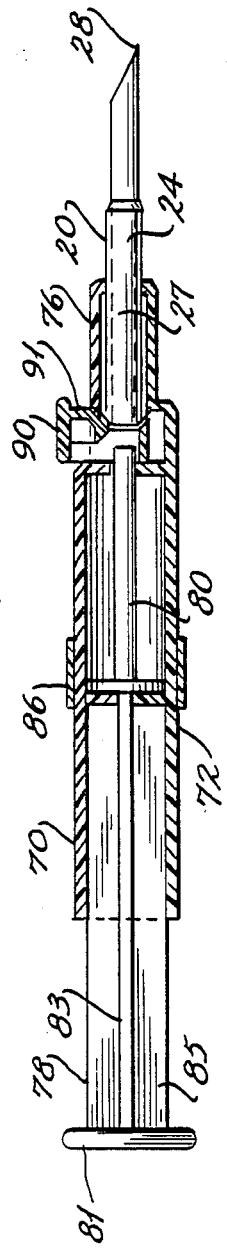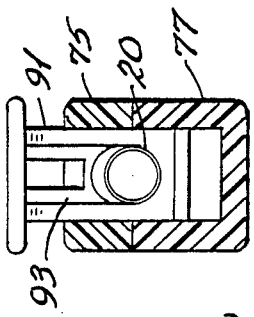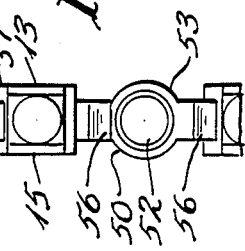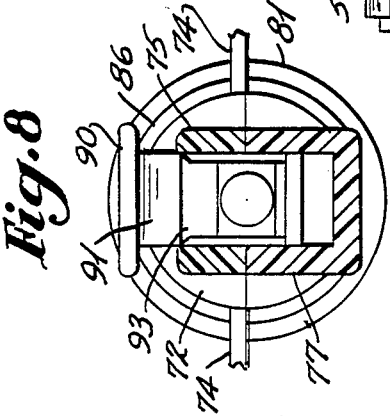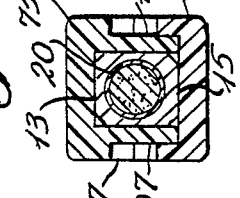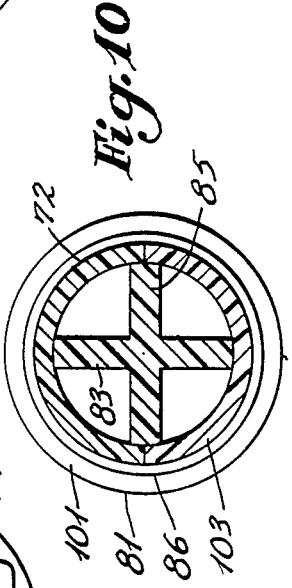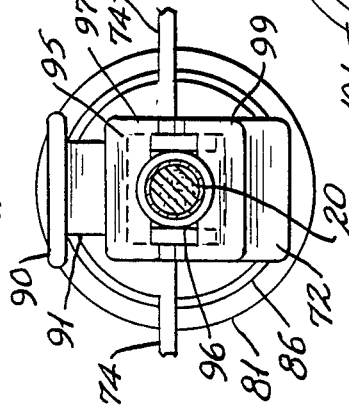

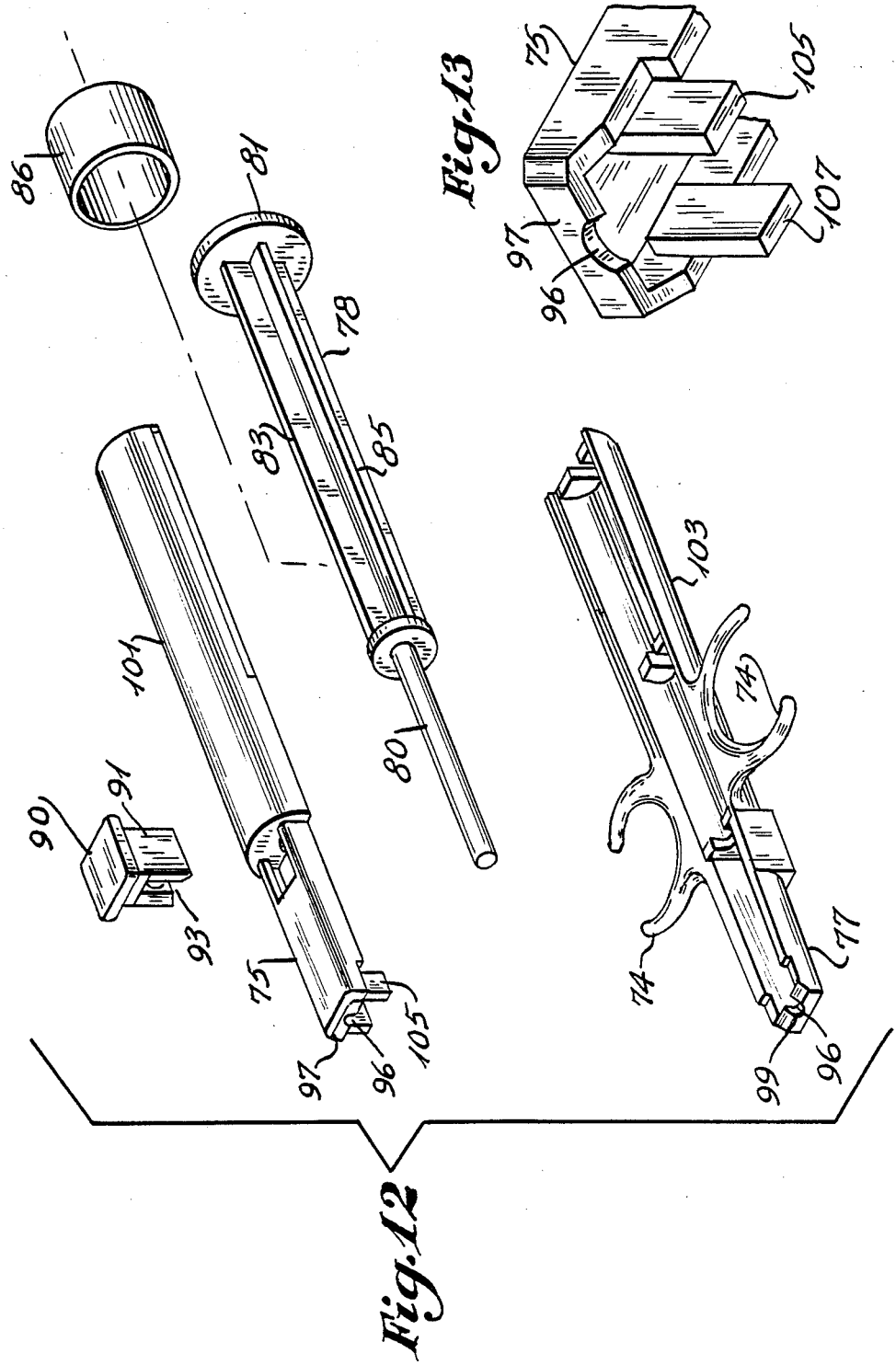

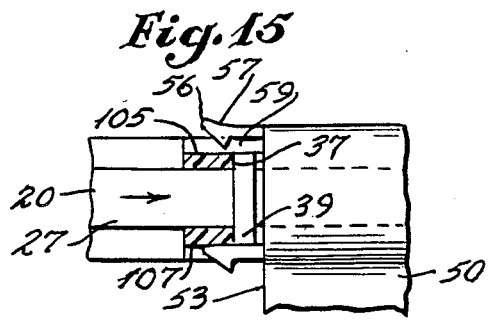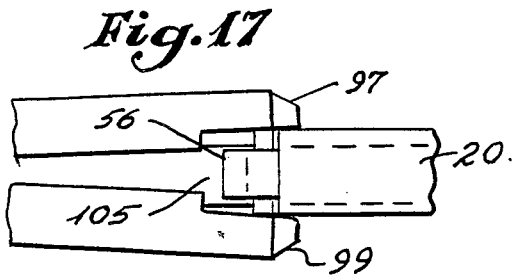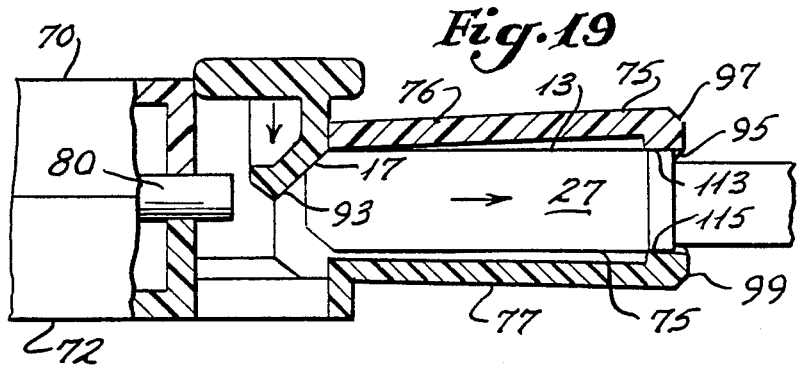

IMPLANTER APPLICATOR

This invention relates to a medicament implant applicator system comprising a needle component, a cartridge for holding a plurality of needles, and an applicator instrument. Each component of the system is of special construction.

INTRODUCTION

Good animal husbandry practice sometimes requires insertion into the animal (e.g., intradermally, subcutaneously, intramuscularly, etc.) of a solid or semi-solid medicament. Such practice is common for growth stimulation of cattle, for example. Solid or semi-solid pellets containing the growth stimulating hormones are implanted in the neck or ear of the animal, to remain there for an extended period, even throughout the life span of the animal. The ear is a preferred implantation site, since the ear is a throwaway organ. Any implant residue present in the ear when the animal is slaughtered never enters channels of commerce, to become ingested by people or domestic animals.

A typical medicament implanter device comprises a handheld instrument built of a size consistent with the size of the animal (large for cattle, small for chickens). An apertured needle on the instrument makes a sizable, non-coring puncture opening into the skin, e.g., of the ear of the animal and forms a cavity in the skin occupied temporarily by the needle on the instrument. The body of the instrument may be shaped like a hand gun, or alternatively, like a hypodermic syringe with a receiver-dispenser for the medicament implant. The needle of the implanter is inserted into the skin of the animal, then withdrawn. As the needle is being withdrawn from the animal, pellets of medicament are expelled into the cavity formed by the needle.

For cattle, an implant dosage unit form may constitute a multiplicity, e.g., eight, relatively small solid or semi-solid pellets. A reciprocal plunger inside the body of the implanter forces the pellet dosage unit out (usually from a cartridge encasement wherein they were prepackaged) into the bore of the needle and from there into the animal.

A number of medicament implant devices have been suggested to the art, including devices adapted for use with cartridges of other encasement forms that contain a multiplicity of dosage units of the implants as, for example, the multi-dose applicators described by U.S. Pat. Nos. 4,531,938 and 4,576,591. This invention relates to a single dose applicator such being an applicator having therein only one dosage unit and in particular to a single dose applicator system comprising a reusable applicator instrument, a disposable needle, and a disposable cartridge containing a plurality of needles. Each needle contains an implant (single dose) dosage unit precharged therein.

DISCUSSION OF THE INVENTION

Many instances exist when the potential user of an implant applicator does not desire to implant a great number of the domestic animals one after another, implanting instead just a few animals at once, or even just one animal from time to time. Multi-dose implant applicators such as those described by the afore-mentioned U.S. Pat. Nos. 4,531,938 and 4,576,591 are not optimum for low levels of usage.

For example, the design of the multi-dose implant applicators known to the inventors hereof inherently includes contemplation that the same needle will be used to implant a multiplicity of animals in rapid succession (on an assumption that the animals are all healthy) and then the needle is cleaned thoroughly or is replaced. Cleaning or replacing the soiled needle becomes a burdensome addition to the implantation procedure when implantation is to be carried on only one animal. A disposable single use needle as is provided in the single dose implant applicator system of this invention constitutes an advantageous convenience.

Associated with the concept of a disposable needle, is the manifest desirability of providing a single use needle that already contains the implant medicament therein, and such a pre-charged needle forms part of this invention. In a sense the needle has become part of the packaging for the medicament. However, a multiplicity of pre-charged disposable needles in boxed up form is not believed to be the best way to provide users with disposable pre-charged single use needles. The present invention comprises in part, a special cartridge for holding therein a multiplicity of the pre-charged needles, from which cartridge advantages hereinafter described result. The needle is of special construction as well.

The implant applicator instrument of this invention is constructed with means thereon to remove a fresh needle from the cartridge, and, after implantation, to reinsert the used needle into the cartridge. Thus, the single use needle can be disposed of safely immediately after use, and a cartridge full of used needles can be discarded as trash without constituting either a hazard or a nuisance.

Advantageously, no part of the implant applicator instrument comes into contact with the wound made by the (disposable) needle during the implantation sequence. Since only a front face on the applicator instrument can be expected even to touch the animal, cleanup after implantation is minimal, something which is particularly advantageous to the user for the occasion when as few as one animal will be implanted during the course of a day.

To repeat, the single dose implant applicator system of this invention requires three specially constructed components: applicator instrument; needle; and, cartridge, each of which is novel, and which together constitute the single dose implant applicator system of this invention.

DESCRIPTION OF THE INVENTION

For further understanding of this invention, reference is made to the attached drawing wherein FIG. 1 is a top plan view of the applicator;
FIG. 2 is a side plan view of the applicator;
FIG. 3 is a front end view of the applicator;
FIG. 4 is a top view in partial section of a cartridge containing precharged needles;
FIG. 5 is a section taken along line 5—5 on FIG. 1;
FIG. 6 is a section taken along line 6—6 on FIG. 1;
FIG. 7 is a section taken along line 7—7 on FIG. 2;
FIG. 8 is a section taken along line 8—8 on FIG. 2;
FIG. 9 is a section taken along line 9—9 on FIG. 2;
FIG. 10 is a section taken along line 10—10 of FIG. 2;
FIG. 11 is a section through the cartridge taken along line 11—11 of FIG. 4;
FIG. 12 is an expanded view of the applicator instrument;

FIG. 13 is an enlarged isometric view of a front end portion of the applicator instrument;

FIGS. 14, 15 are partial top views and FIGS. 16, 17 are partial side plan views of the cartridge and needle that illustrate how the needle removal and insertion sequence is carried out;

FIGS. 18 and 19 are partial side sections of the applicator instrument that illustrate how the needle is released from the applicator instrument; and FIG. 20 is a top plan view section of the needle and contents.

THE NEEDLE

As may be seen in FIGS. 1 and 20, the disposable needle component which forms part of this invention comprises a hollow needle member 20 shaped as hereinafter described. Desirably, needle 20 is a unitary molded piece made from a rigid (commercially available) plastic, e.g., polycarbonate. The material for construction for needle 20 forms no part of the present invention. Suffice it to point out that moldable plastics from numerous resins and resin combinations capable of being formed into hard and tough molded needles are commercially available, including some, e.g., polycarbonate, that may be formed with a needle point 28 sharp enough and sturdy enough to penetrate the skin of a calf. Specific materials that have been found suitable for needle 20 are Lexan TM (General Electric).

A disposable pre-charged needle sub-assembly comprises one aspect of this invention. Included in the sub-assembly are needle 20, cylindrical medicament pellets 22 and cylindrical retention pin 30. The pellets and retention pin fit inside needle bore 24.

The medicament pellets 22, which may, for example, be a growth promoting composition, constitutes whatever medication will be applied to the animal. The medicament pellets per se form no part of this invention. As a practical matter the medicament pellets may be the very same medicament pellets employed in the multi-dose implant applicators heretofore used in the art. The medicament pellets 22 slidably fit in the bore 24 of needle 22, being retained therein behind point 28 of the needle and ahead of retention pin 30.

As is illustrated by FIG. 20, the bore 24 of needle 20 is stepped front to rear; the bore diameter at forward end portion 21 of needle 20 (wherein the medicament pellets slidably rest) is smaller than the bore diameter in the rear end portion 23, being, for example, 0.130" and 0.140" respectively. At the forward end of needle 20, a further reduction in the internal diameter is provided, e.g., to 0.125", through provision of a rounded section 25. The diameter reduction is just enough to prevent the medicament pellets 22 from sliding out past needle point 28, but near enough to the diameter of the pellet to allow an impeller to force the pellets (which are somewhat soft and deformable) through the reduced diameter of rounded section 25 and out past needle point 28. Dimples (in the needle bore) or like expedients may be employed instead of the rounded section 25 illustrated by the drawing.

Retention pin 30 is formed with a stepped outer diameter. The front end section 31 of pin 30 is sized, e.g., 0.120" to slidably fit inside the forward end portion 21 of needle bore 24, and also to pass the reduced in diameter part rounded section 25 adjacent the front of the needle bore. However, the larger diameter rear end section 33 of retention pin 30, e.g., 0.135" is of a size to slidably fit only in the (wider) rear end portion 23 of needle bore 24.

The retention pin 30 serves as a (rear) plug element or a drive pin for medicament pellets 22 retaining them inside needle bore 24, and in particular in the forward end portion 21 of the needle bore. In an exemplary embodiment retention pin 30 is 1.5" long, of which the stepped down section 31 is 1.25" long. Thus retention pin 30 extends in needle bore 24 from the rear thereof to the stepped down portion thereof, serving thereby to retain medicament pellets 22 entirely in forward end portion 21 of the needle bore 24. FIG. 20 of the drawing, though not strictly to scale, generally illustrates the relative proportions and sizes of needle 20, retention pin 30 and medicament pellets 22.

The retention pin 30 is intended to be retained inside needle bore 24, e.g., through a friction fit between the rear end sections 33 and 23 of pin 30 and needle bore 24 respectively. If manufacturing tolerances are somewhat loose and a proper frictional engagement between (mass produced) pins and needles is not certain, a dimple may be formed (at the needle bore) in the shank face of needle 20 to keep retention pin 30 from sliding out the rear of needle 20. Desirably, retention pin 30 may be molded from a modestly elastic commercially available plastic such as low density polyethylene.

Retention pin 30 has been shaped to act as a (disposable) impeller element for expulsion of the medicament pellets 22 from needle 20. When pushed from the rear by an impeller rod that forms part of the implanting applicator instrument hereinafter described, the retention pin 30 is advanced in needle bore 24 until the wider rear end section 33 of the retention pin reaches the narrower front end of the needle bore, seizes there and can advance no further. By then, however, all of the medicament pellets 22 have all been expelled from needle 20. At the seizure point the front tip of retention pin 30 extends just beyond needle point 28, e.g., by 0.250", ensuring thereby that all of the medicament pellets have cleared the needle 20 to become deposited in the needle track.

It is noted that in the multi-dose applicator modes known to the inventors hereof, such as the applicator illustrated by U.S. Pat. No. 4,576,591, an impeller element therein must advance in some part beyond the needle point to expel the pellets. Doing so brings the tip of the impeller into contact with the animal body fluids in the needle track, soiling same and generating thereby the risk of cross-contamination from one animal to the next animal. The impeller element, and probably the multi-dose applicator as a whole should be cleaned (sterilized too) after completion of a multi-animal implantation sequence. The disposable single use needle sub-assembly of the present invention uses retention pin 30 for expelling medicament pellets 22 from needle 20. The forward tip of retention pin 30 comes into contact with the animal body fluids of the animal track, but then retention pin 30 remains with needle 20. Accordingly, employment of retention pin 30 as a one-time use disposable impeller element is an advantageous feature of this invention.

FIG. 20 of the drawing also illustrates the structural features provided on needle 20 for orienting and mounting the needle sub-assembly in cartridge 50 and in the implant applicator instrument 70.

As may be seen in the drawing, the shank portion 27 hereinafter termed shank 27 of needle 20 is angular being square or rectangular in cross-section, the latter being preferred, e.g., ¼"×3/16". The forward portion 29 of needle 20, is preferably circular, but may be elliptical in cross-section, the term rounded being employed hereinafter, and can be stepped down with a narrower section thereon before terminating in an acute angle taper cut (e.g., at 24°) and, of course, the needle point 28. The tapered front end of needle 20 constitutes an orienting mean that positions needle 20 properly into a correspondingly tapered close fitting blind hole socket 52 in cartridge 50 at the desired attitude, see FIG. 4.

The angular shank 27 has a narrow flange 37 at the forward end thereof, the purpose of which is to serve as a retaining means for securing the needle 20 in cartridge 50. Flange 37 upstands from one shank face 9; a like flange 39 upstands from the opposing shank face 11; the other two shank faces 13, 15 are blank faces, see FIGS. 18, 19. The needle 20 is oriented in cartridge by the fit of the acute angle taper cut behind needle point 28 with a corresponding taper in the cartridge socket 52 wherein the needle seats so that the flange 37 becomes properly oriented vis a vis cartridge 50.

It is noted that the outer surface of needle 20 contains an abrupt transition from angular shank 27 to the rounded forward section 29 of needle 20. The cross-section area of the angular shank 27 of needle 20 is greater than the rounded cross-section area of the forward section 29 of needle 20 (without taking flanges 37, 39 into account) as may be seen on FIGS. 11 and 20. As will be described in detail hereinafter, angular shank 27 on needle 20 fits into a recess on applicator instrument 70 and a pair of jaws on the applicator instrument close over blank shank faces 13, 15 and also flanges 37 and 39 to lock the shank 27 in the applicator instrument 70.

The shank 27 terminates in a bevelled rear face on which the bevel 17, (e.g., a 45° bevel), constitutes a cam surface employed to spread the aforementioned jaws on applicator instrument 70 enough to enable them to encompass blank shank faces 13, 15 when a needle 20 is inserted into the applicator instrument 70; see FIGS. 16 and 19.

THE CARTRIDGE

Reference is now made to FIGS. 4, and 11, whereon may be seen the details of cartridge 50, which is a molded plastic member, e.g., of low density polyethylene. Cartridge 50 provides the packaging unit for a reasonable number of needles, e.g., ten. (An eleventh slot, as illustrated in the drawing may be provided for holding a used needle from a previously used cartridge.)

The cartridge 50 is thin relatively elongated, somewhat like a parallelepiped, and contains a multiplicity of blind hole sockets 52 extending in from a narrow face 53, which face is termed the front face 53 of the cartridge. In the embodiment illustrated herein the side faces of cartridge 50 appear ribbed (at socket 52). Extending forward of front face 53 of cartridge 50 between the socket openings, are a multiplicity of hooks 56, so that a hook faces each socket. The prong 57 of hook 56 extends (down) toward the axis line of the adjacent, socket 52. A narrow rectangular channel 59, e.g., 3/32" wide 3/64" deep, is formed between prong 57 and the front face 53 of cartridge 50.

The channel 59 provides a (modestly oversized) seat for the flange 37 on the shank 27 of needle 20, as is illustrated in FIG. 4. The hook 56, through its prong 57 and channel 59 wherein needle flange 37 seats serves to lock needle 20 inside socket 52. The hook 56 must be flexed away from (the axis line of) its adjacent socket 52 to allow insertion and/or removal of needle 20 from the socket 52 and cartridge 50, see FIG. 15. (Mention already has been made that cartridge 50 is molded from a resilient plastic such as low density polyethylene). During the removal and/or reinsertion of a needle into cartridge socket 52 force is applied against the beveled face 61 on prong 57, which force causes the resilient plastic of prong 57 to flex away from its associated socket 52 enough to allow the flange 37 on needle 20 to clear prong 57 (e.g., 3/64"). Movement of prong 57 allows needle 20 to be introduced or withdrawn from cartridge 50. Thus, the bevel face 61 on prong 57 serves as a cam surface. A fang to be described hereinafter that forms part of the implant applicator instrument 70 comes into camming contact with bevel face 61 (to force prong 57 and hook 56 as a whole to flex away from its associated socket 52).

As has already been pointed out, the forward end portion of each socket 52 is configured (to fit the tapered cut at needle point 28) so that seating needle 20 fully in socket 52 orients needle 20 so as to position the flange 37 at and in channel 59, see FIG. 4. The fit of needle 20 in socket 52 allows the forward faces of flanges 37, 39 to seat flush against front face 53 of cartridge 50, thus leaving a gap, e.g., 1/64" between prong 57 and flange 37. To repeat, channel 59 is wider than flange 37.

The width of the needle shank between the blank opposing surfaces 13 and 15 on the shank portion 27 of needle 20, e.g., .250" is desirably about the same as the cartridge width (at socket 52), i.e., at a rib of cartridge 50, as is illustrated in FIG. 11. On the whole, the needle shanks form a squared off essentially flush extension to cartridge 50, and such may be seen in FIGS. 4 and 11.

IMPLANT APPLICATOR

Reference is now made to FIGS. 1, and 5 wherein is shown the implant applicator instrument 70 with a needle 20 mounted therein and to the exploded view of FIG. 12. The applicator instrument 70 comprises a cylindrical handle 72 on which (finger) grips 74 may be disposed; a movable plunger 78 extends from the rear of handle 72 and a nose 76 extends forward of the handle 72. Nose 76 is adapted to receive therein the shank 27 of needle 20 and retain same firmly so that the pre-charged medicament can be expelled through needle point 28.

Expulsion of the medicament pellets from needle 20 is accomplished out by pushing plunger 78 forward; an impeller rod 80 (see FIGS. 5 and 12) which is an extention of plunger 78 constitutes the element which impinges upon retention pin 30 and thereby forces expulsion of medicament pellets 22 from needle 20. In the embodiment of implanter instrument 70 herein illustrated, the plunger 78 is a molded component which comprises a rear face 81 (for gripping purposes), a pair of wings 83, 85 generative of a cruciform in cross-section shape as shown best in FIG. 10, the impeller rod 80 being a forward extension (of the intersecting region) of wings 83, 85. Plunger 78 extends to the rear of handle 72 the distance traveled by impeller rod 80 for causing explusion of medicament pellets 22 from needle 20.

FIG. 5 illustrates how wings 83 and 85 slide along the inside wall of cylindrical handle 72 so as to guide and center impeller rod 80 to bore 24 through needle 20. Impeller rod 80 pushes retention pin 30 forward to the aforementioned seizure point inside bore 24, expelling medicament pellets 22. The distance that can be traveled by plunger 78, is, of course, related exactly to the distance that can be travelled by retention pin 30 and all significant axial dimensions in handle 72 are in correspondence therewith. Thus, in the herein illustrated embodiment the plunger 78 comes to rest against a back surface on handle 72 exactly when the distance to the seizure point has been traveled. Handle 72 acts as a stop element for plunger 78, just like the step down constriction in needle bore 24 (i.e., the seizure point) acts as a stop element for retention pin 30. It may be noted that (at full retraction of plunger 78), the dimensions selected should provide a (small) gap between the forward end of impeller rod 80 and the rear of needle 20. Presence of a gap facilitates introduction of needle 20 into and removal from implanter instrument 70.

It can be appreciated that impeller rod 80 has been allowed only partial penetration into needle bore 24, e.g., a 1 ¼" penetration into a 2½" needle, and therefore impeller rod 80 has been effectively isolated from contact with the (needle track) wound of the animal being implanted.

Adjacent the juncture of handle 72 and nose 76 of the applicator instrument 70, e.g., on nose 76 at the base end thereof, is a button 90 with a stem 91 that moves radially inward (although not necessarily exactly radially) into the gap between needle 20 and impeller rod 80. Stem 91 has a bevel face 93 thereon. Button 90 forms part of the needle insertion and removal mechanism in the applicator instrument 70, and this mechanism now can be described.

When applicator instrument 70 contains a needle 20 therein as is illustrated in FIGS. 1, 2, and 5, the shank 27 of needle 20 has become encompassed inside nose 76 with bevel 17 on end face of shank 27 flush against bevel face 93 on the stem 91 of button 90, and with flat side faces 13, 15 and the front face of shank 27 flush against the inside walls of nose 76 as is illustrated in FIGS. 5 and 18. Needle 20 is locked in place. To remove needle 20 from applicator instrument 70, nose halves 75, 77 are spread apart (as will be described hereinafter), then pushing button 90 (radially inward) will act to partly expel needle 20 from nose 76, see FIG. 19.

As is indicated in FIG. 12, handle 72 is formed from a pair of matching molded members 101, 103 joined together by a retaining ring 86 just behind the finger grip 74. A pair of extensions 75, 77 that form part of the otherwise hemicylindrical members 101, 103 respectively constitute the nose 76. At their forward end those extensions or nose halves 75, 77 dip toward each other, as is better seen in FIGS. 18, 19 so as to provide nose face 95. In detail, nose face 95 comprises a pair of rounded spaced apart jaws 97, 99 opposing one another with flat internal surfaces 113, 115 against which the forward end face of needle shank 27 seats, see FIGS. 18 and 19. Between jaws 97, 99 is an aperture 96 of shape and size to encompass the rounded portion 29 of needle 20 just forward of shank 27. It is noted that the jaw surfaces that bound aperture 96 are themselves rounded off so that they may act as cam surfaces. Flanges 37, 39 on needle shank 27 fit into slots between jaws 97, 99.

Inside nose 76 is a recess adapted to encompass shank 27 of the needle, with internal flat walls on nose halves 75, 77 in contact with the (flat) unflanged faces 13, 15 of shank 27, the side flanged faces 9, 11 of shank 27, and the rear bevelled face of shank 27 in contact with a bevel 93 on stem 91 of button 90. The flanged faces of shank 27 are at the split between nose halves 75, 77 with the flanges partially encompassed by nose halves 75, 77.

Extending laterally from nose half 75 into the space between nose halves 75, 77 are fangs 105, 107, see FIG. 13. Fang 105 is employed during removal from and during reinsertion of needle 20 into cartridge 50, but forms no part of the needle retaining structure in nose 76.

The relatively lengthy finger-like nose halves 75, 77 are free to flex apart, pivoting principally around their junctures with handle 72 when and as a lateral force (spreading them apart) is applied against the jaws 97, 99 of nose face 95. The fangs 105, 107 normally are concealed within the nose 76, but become exposed when nose halves 75, 77 are spread apart.

To mount a needle 20 in an empty applicator instrument 70, a procedure illustrated by FIGS. 14–17 the applicator 70, is first oriented so that the split between nose halves 75, 77 and therefore between the jaws 97, 99 is in line with thin front face 53 of cartridge 50 as is shown in FIG. 14. Then when jaws 97, 99 are pushed against the shank end of a needle 20, jaws 97, 99 are cammed apart by the bevel 17 at the base of needle shank 27 sufficiently to allow shank 27 to enter through the aperture 96 between jaws 97, 99. The cammed apart nose halves 75, 77 then ride over the flat faces 13, 15 of the shank and jaws 97, 99 slide past shank 27 onto the cartridge top and bottom face surfaces. The fang 105 which is located on nose half 75 behind jaw 97 becomes exposed, see FIGS. 13, 15, 17. Fang 105 acts to cam prong 57 away from its associated socket on cartridge 50 as the spread apart jaws 97, 99 ride past shank faces 13, 15 onto the cartridge. Finally, the applicator 70 has been pushed against needle 20 and cartridge 50 until the bevel 17 on the rear face of needle 20 is stopped by bevel face 93 on the stem 91 of button 90. Hook 56 has been cammed clear of flange 37.

Once shank portion 27 is fully encompassed with jaws 97, 99 on the cartridge top and bottom face surfaces, the forces which applicator instrument 70 impose on cartridge 50 and needle 20 change. Up to this point needle 20 and cartridge 50 act as an integral unit in opposing (the needle encompassing) force applied by applicator instrument 70. Then the back side rounded surfaces on the jaws 97, 99 of the applicator nose face 95 contact the forward face of needle shank 27 (to the extent allowed by the cartridge thickness at socket 52) generating a force at the juncture of the needle shank 27 and cartridge 50 which would act to drive the shank portion 27 deeper into nose 76 and also to push cartridge 50 away from applicator instrument 70. The needle cannot move yet because the applicator instrument 70 is still pressed against the cartridge 50. However, withdrawal of applicator instrument 70 from cartridge 50 will now remove needle 20.

During initial withdrawal movement, fang 105 retains prong 57 in the cammed away location that will release the needle flange 37 from channel 59, and allow flange 37 to clear the prong 57 and needle 20 is moved from flush against cartridge 50 to flush against fangs 105 and 107 at the needle shank flanges 37 and 39 respectively as is illustrated in FIG. 15. Then as applicator 70 (and needle 20) is being withdrawn further from cartridge 50 the jaws 97, 99 on nose 76 close behind the front of shank 27 and in so doing urge needle shank 27 back against the button bevel face 93. During withdrawal fang 105 and flange 37 present an essentially continuous surface to prong 57 so that (on withdrawal) prong 57 rides over fang 105 then over flange 37, as can be seen from FIG. 15. Only after flange 37 clears hook 56, can jaws 97, 99 fully close behind the front of shank 27 so as to lock the needle shank 27 inside nose 76 as is illustrated in FIG. 18. The flat portions on the back faces of jaws 97, 99 rest on needle shank faces 13, 15. The bevel face 93 on button stem 91, now in contact with needle bevel 17, serves as back stop and the flat rear faces 113, 115 of nose jaws 97, 99 serve as the front stop. Thus, needle 20 has become integrally secured to nose 76 and to implanter instrument 70 as a whole.

The medicament applicator of this invention is employed much like those of prior art applicators, e.g., like the applicator instrument described by U.S. Pat. No. 4,531,938. In specific, the needle 20 is fully inserted into the skin of the animal to be implanted, then while the needle is being withdrawn, plunger 78 is advanced, advancing thereby the impeller rod 80 into needle bore 24, see FIG. 18. In turn, this forward movement of impeller rod 80, advances retention pin 30 through needle bore 24, thereby expelling medicament pellets 22 into the needle track. At full advancement of impeller rod 80 the retention pin 30 has been pushed to its seizure point, and its tip end then extends just beyond needle point 28 as shown in FIG. 20. When the plunger 78 is retracted, retracting impeller rod 80, the retention pin 30 usually remains behind in its advanced position, being held there by its seizure against the wall of needle bore 24. The used needle may then be removed from implanter instrument 70 by insertion of the needle into a vacant socket 52 on the cartridge 50.

The used needle 20 must be inserted into a vacant socket 52, with needle point 28 properly oriented vis a vis the socket hole, or else, all of rounded shaft portion 29 of needle 20 cannot be encompassed inside socket 52. When needle 20 is properly oriented in its socket 52, nose jaws 97, 99 of applicator instrument 70 are oriented so they may ride up over the cartridge side walls as before.

When nearly all of the rounded front portion 29 of needle 20 has been introduced into socket 52 the face 95 on applicator nose 76 strikes cartridge front face 53 at the rounded front surfaces adjacent the aperture 96 between jaws 97, 99. Through camming contact the jaws are spread apart until they encompass cartridge face 53 and on continued advance of applicator instrument 70 the applicator jaws 97, 99 ride over onto the side walls of cartridge 50. As before (i.e., when a needle is to be removed from cartridge 50), prong 57 is cammed away from its adjacent socket by (flange 37 and) fang 105 so that the flange 37 on needle 20 clears hook 56. The flange 37 enters the space of channel 59 and comes to rest flush against the cartridge front face 53. Then, needle 20 has become fully inserted into socket 52.

At this time the button 90 is depressed causing bevel 93 on button stem 91 to cam the needle shank 27 forward vis a vis applicator instrument 70 as is illustrated in FIG. 19. Ordinarily, this camming action would cause longitudinally forward movement of needle 20 (through the camming action of button bevel 93 on bevel 17 of the needle shank face). Since needle 20 is being pressed fully into its socket 52, with flange 37 flush against front face 53 of cartridge 50, the camming force applied by the button stem 91 causes also, a small retraction movement of applicator instrument 70 away from the front face 53 of cartridge 50 to the position of flange 37 in channel 59 shown in FIG. 14. This small retraction movement of applicator instrument 70 moves the spread apart jaws 97, 99 back off the cartridge top and bottom side surfaces onto (the blank) shank faces 13, 15 of needle 20, and generates a gap between fang 105 and needle shank flange 37. In addition, the fang 105 is withdrawn from camming contact with prong 57 at its bevel face 61. As fang 105 withdraws, prong 57 flexes toward its normal location, entering into the gap that has been generated between fang 105 and needle flange 37. It is to be noted that flange 37 is then spaced apart from prong 57 since channel 59 has been made slightly oversized (e.g. by 1/32").

Thus, although the needle shank 27 is still pressed flush against the cartridge face by applicator instrument 70, the applicator instrument 70 as a whole has withdrawn from cartridge 50 a sufficient distance to allow a return of prong 57 toward its unflexed position sufficient to hook flange 37 inside of channel 59. With shank flange 37 locked in channel 59, further withdrawal of applicator instrument 70 from cartridge 50, causes the jaws 97, 99 on applicator nose 76, to ride back over the blank shank faces 13, 15, and an empty applicator instrument 70 is removed from cartridge 50.

From the foregoing description of the implanter applicator system and of its operation, it should be apparent that the system as a whole is well adapted to occasional or even frequent single use and, advantageously, reduces certain concerns that are inherent in the very concept of single use. The disposable needles are stored inside the cartridge relatively free from possible contamination until removed one by one for use, and the empty disposable needles become collected in the cartridge, a cartridge loaded with used needles being a much more convenient discard item than ten or so separate needles (and an empty cartridge).

We claim:
1. A medicament implanter comprising:
   (a) a hollow disposable needle pre-charged with a medicament implant dosage unit and an implanter instrument whereon said disposable needle is temporarily mounted, said implanter instrument having as components thereof an impeller rod movable into and out of said needle and means for moving said impeller rod, impeller movement serving to expel the implant dosage unit from said needle;
   (b) said needle being formed with a rectangular or square in cross-section shank, a rounded in cross-section front portion of area smaller than the shank cross-section area, and an abrupt transition between shank and front portion; and
   (c) said implant instrument being formed at the front end thereof with a pair of opposed jaws adapted to lock the shank of said needle in a recess between and behind said jaws, said jaws being spreadable enough to receive and to release said needle from the recess,
   said implant instrument further comprising a movable cam means mounted on said instrument at the rear of said opposed jaws, said cam means being positioned for needle expelling contact with the rear face of the shank of said needle, whereby movement of cam means may expel said needle at a time the jaws are spread apart.

2. A medicament implanter instrument adapted for use with a hollow disposable needle pre-charged with a medicament implant dosage unit, said needle being formed with a rectangular or square in cross-section shank, a rounded front portion of area smaller in cross-section area than the shank cross-section area, and an abrupt transition between the shank and front end portion, said instrument having as component parts thereof:
- (a) an impeller rod and a plunger means for moving said impeller rod, said impeller rod being movable into and out of the above described pre-charged disposable needle when such a needle is temporarily mounted in and secured to said instrument so as to expel the implant dosage unit from said needle,
- (b) a pair of opposed jaws formed at the front end of said instrument adapted to lock the shank of a disposable needle as aforesaid in a recess between and behind said jaws, said jaws being spreadable enough to receive and to release the needle,
- (c) said implant instrument further comprising a movable cam means mounted on said instrument at the rear of said opposed jaws, said cam means being positioned for needle expelling contact with the rear face of the shank of a needle as aforesaid whereby movement of said cam means may expel said needle at a time the jaws are spread apart.

3. A medicament implanter instrument as in claim 2 further comprising a cylindrical handle, the movable plunger means being to the rear of said handle, the impeller rod being inside of said handle, and a nose forming part of said implanter instrument extending forward of said handle the nose being comprised of two nose halves with one of said jaws at the forward end of each nose half, said jaws being spreadable through deflection of the nose halves, and said recess being between the nose halves.

4. A medicament implanter as in claim 3 wherein said handle further comprises a pair of molded handle halves each said nose half being integral with an extension of a handle half.

5. A medicament implanter instrument as in claim 2 wherein said cam means also constitutes a rear stop element for such a needle in said recess.

6. A disposable needle for implanting medicament which comprises a hollow elongated needle said needle having a rounded in cross-section front portion that terminates in an acute angle cut generative of a sharp needle point, and capable of serving as a means to orient said needle in a cartridge socket formed as a blind hole with a like acute angle terminus,
said needle having a rectangular or square in cross-section shank larger in cross-section area than the rounded in cross-section front portion, and having an abrupt transition between shank and front portion, and
an upstanding flange on at least one surface of said shank adjacent said transition, said flange being adapted to serve as a locking means for retaining said needle in a cartridge socket, an opposing pair of unflanged surfaces being on said shank thereof adjacent said flanged surface,
said needle further comprising a bevelled end face on the shank of said needle, the bevel of the end face being adapted to serve as a cam surface during removal of the needle from needle receptor means of a medicament implanter instrument.

* * * * *